United States Patent [19]

Koshiishi

[11] 4,305,802
[45] Dec. 15, 1981

[54] COMPOUND CHEMICALLY SENSITIVE ELEMENT

[75] Inventor: Kiyozo Koshiishi, Sagamihara, Japan

[73] Assignee: Olympus Optical Co., Ltd., Japan

[21] Appl. No.: 147,708

[22] Filed: May 8, 1980

[30] Foreign Application Priority Data

Aug. 10, 1979 [JP] Japan .......................... 54/101321

[51] Int. Cl.$^3$ ............................................ G01N 27/30
[52] U.S. Cl. ............................... 204/195 M; 128/635;
204/195 R; 204/195 P; 204/195 B; 204/195 S; 357/25
[58] Field of Search ......... 357/25; 204/195 R, 195 M, 204/195 B, 195 P, 1 E; 128/635

[56] References Cited

U.S. PATENT DOCUMENTS 4,020,830  5/1977  Johnson et al. ............... 357/25 X
4,218,298  8/1980  Shimada et al. ............... 357/25 X

FOREIGN PATENT DOCUMENTS 52-26292  2/1977  Japan ........................... 204/195
54-66092  5/1979  Japan ........................... 204/195

*Primary Examiner*—G. L. Kaplan
*Attorney, Agent, or Firm*—Ostrolenk, Faber, Gerb & Soffen

[57] ABSTRACT

A compound chemically sensitive element comprises a chemically sensitive assembly which is selectively sensitive to a specific ion or a specific substance in a material to be examined, and a pH sensor having an insulated gate field effect transistor structure, both of which are separately manufactured. The chemically sensitive assembly and the insulated gate of the pH sensor are electrochemically connected together by a conductive resin, thus improving the durability and the selectivity of the element. In this manner, limitations imposed upon the manufacture of MOS pH sensor is removed, permitting a wide variety of chemically sensitive films to be used.

14 Claims, 5 Drawing Figures

COMPOUND CHEMICALLY SENSITIVE ELEMENT

BACKGROUND OF THE INVENTION

The invention relates to a compound chemically sensitive element, and more particularly, to such element which may be used to determine the concentration of a specific ion or other specific substance contained in a solution to be examined such as blood serum.

As is recognized, an ion sensor having a selective ion sensitive electrode is used in a determination of the concentration of a specific ion in an electrolytic solution. A glass electrode which is used in a pH meter is a typical example. An ion sensor having a selective ion sensitive electrode advantageously permits a continuous determination of the concentration of a specific ion in an electrolytic solution in a very simple manner by merely immersing the sensor directly into the solution to determine an electric potential.

Recently, with an increasing demand on the miniaturization of such ion sensor, a variety of chemically sensitive elements have been proposed which comprise a chemically sensitive film of one kind or another formed on the gate of an insulated gate field effect transistor (IGFET). (cf. IEEE Transactions on Biomedical Engineering, Vol. BME-19, No. 5, September 1972, an article by P. Bergveld on page 342.) A chemically sensitive element which is based on the principle of such IGFET element is generally referred to as ion sensitive field effect transistor (ISFET). A variety of chemically sensitive elements are available which are capable of detecting the presence of various ions and other substances depending on the kind of a chemically sensitive film which is applied to the gate thereof.

By way of example, Japanese Laid-Open Patent Application No. 26292/1977 discloses a pH sensor comprising $SiO_2$-SiN applied to the gate of a MOS (metal oxide semiconductor) transistor. The pH sensor can be manufactured utilizing a conventional process of manufacturing a semiconductor device, and hence is easily manufactured. It exhibits an excellent functionability and durability. Various ion sensors are proposed which comprise the pH sensor having $SiO_2$-SiN layer applied to its gate and having an ion sensitive film which is responsive to a specific ion formed on the layer.

An ion sensitive film conventionally used in the art of ion selective electrodes comprises a high melting glass film, but it is very difficult to apply such film to the gate of ISFET to which $SiO_2$-SiN layer is already formed. For example, a film which is sensitive to $Na^+$ comprises soda aluminosilicate glass (11% $NaO_2$—18% $Al_2O_3$—71% $SiO_2$), and has a high viscosity as well as a vitrifying temperature which is as high as 1,300° C. or even higher. It will be seen that it will be very difficult to form such an ion sensitive film directly on the gate of MOS transistor as by chemical vapor deposition (CVD) or sputtering without destructing the function of the transistor. To accommodate for this difficulty, metal alcoholate is utilized to form a solution having a given proportion of glass components, and the solution is uniformly applied to the upper surface of $SiO_2$-SiN layer on the gate of ISFET either by spraying, coating, dipping or like process. Subsequently, it is heat treated at a low temperature which is equal to or below 500° C. to form an ion sensitive film. However, the film formed according to this process has a durability which is greatly inferior to that of soda aluminosilicate glass which is used as $Na^+$ sensitive film or soda aluminosilicate glass (27% $NaO_2$—5% $Al_2O_3$—68% $SiO_2$) which is used as $K^+$ sensitive film. For these reasons, an ion sensor having an ion sensitive film formed on the gate of ISFET which comprises $SiO_2$-SiN layer is limited in the choice of material which forms the ion sensitive film, and exhibits a durability and ion selectivity which are less than desired.

To eliminate such disadvantages of the conventional ion sensor, the present applicant has previously proposed an ion sensor in which an ion sensitive assembly which is sensitive to a specific ion in a solution to be examined and the insulated gate of a pH sensor are electrochemically connected together by an electrolytic solution or a gel-like material containing an electrolyte (see Japanese Patent Application No. 66,092/1979). With this ion sensor, the ion sensitive assembly can be manufactured separately from the pH sensor, and hence its manufacture is facilitated. In addition, any known material having excellent durability and ion selectivity may be freely used for the ion selective film. However, in the disclosed ion sensor, the connection of the ion sensitive assembly with the insulated gate of the pH sensor by means of an electrolytic solution or a gel-like material containing an electrolyte prevents stable use over a prolonged period of time due to the evaporation or desiccation of the electrolytic solution or the gel-like material. Thus, after a given period of use, the electrolytic solution or the gel-like material must be replenished, resulting in troublesome maintenance and control. Also, in the actual determination, the ion sensitive assembly and the insulated gate of the pH sensor must be positively connected together by the electrolytic solution or the gel-like material at the same time as the ion sensitive assembly is brought into contact with a solution to be examined, and this limits the orientation in which the ion sensor is disposed, again resulting in a troublesome handling.

SUMMARY OF THE INVENTION

It is an object of the invention to provide a compound chemically sensitive element in which an ion sensitive assembly which is sensitive to a specific ion upon contact with a solution to be examined and the insulated gate of a pH sensor having an insulated gate field effect transistor structure are electrochemically connected together by a conductive resin.

It is another object of the invention to provide a compound chemically sensitive element in which a chemically sensitive assembly which is sensitive to a specific substance upon contact with a material to be examined and the insulated gate of a pH sensor having an insulated gate field effect transistor structure are electrochemically connected together by a conductive resin.

In accordance with the invention, the chemically sensitive assembly and the pH sensor are separately manufactured, and the chemical sensitive assembly and the insulated gate of the pH sensor are electrochemically connected together by a conductive resin. As a result, the need for a heat treatment which may be required when the chemically sensitive assembly is directly formed on the insulated gate is substantially eliminated, avoiding any likelihood that the function of the pH sensor may be degraded.

In addition, it is possible to use any known glass film or solid film directly as an ion sensitive assembly, thereby facilitating the manufacture of the chemically sensitive element. In addition, there is obtained a chemically sensitive element having an excellent durability and selectivity.

As compared with the direct application of the ion sensitive film upon the insulated gate of the pH sensor, the chemically sensitive assembly of the invention may have an increased surface area, reducing the film resistance of the chemically sensitive assembly and noises to permit a high accuracy of measurement to be achieved.

Finally, since the material which provides an electrochemical connection between the ion sensitive assembly and the insulated gate of the pH sensor comprises a non-volatile conductive resin, the maintenance and control is facilitated. Also the orientation in which the compound chemically sensitive element is disposed may be freely chosen, simplifying its handling.

DESCRIPTION OF PREFERRED EMBODIMENTS

Figure 1:
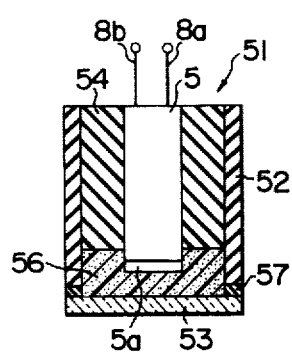
FIG. 1 is a cross section of a compound chemically sensitive element constructed as an ion sensor according to one embodiment of the invention.

FIG. 1 shows a compound chemically sensitive element according to an embodiment of the invention. Specifically, a compound chemically sensitive element 51 comprises an outer highly insulating sleeve 52, an ion sensitive film 53 applied to the lower end face of the sleeve 52 with an insulating resin 57 so as to close the bottom opening, a pH sensor 5 fixedly connected to the inside of the sleeve 52 with an insulating resin 54 so that its insulated gate 5a is located downside, a conductive resin 56 which fills the space within the sleeve 52 between the ion sensitive film 53 and the resin 54 so as to contact the insulated gate 5a, and a pair of lead wires 8a, 8b connected to the pH sensor 5.

The ion sensitive film 53 is not directly mounted on the insulated gate 5a of the pH sensor 5, and is hence subject to no restriction during its manufacture. Consequently, any known ion sensitive film may be directly used as the film 53. By way of example, the soda aluminosilicate glass having the composition mentioned previously may be used as Na+ sensitive film, and the soda aluminosilicate glass having the described composition may be used as K+ sensitive film. A solid film comprising a mixture of silver chloride (AgCl) and silver sulfide (Ag$_2$S) may be used as Cl− sensitive film. Alternatively, a solid film comprising lanthanum fluoride LaF$_3$ may be used as F− sensitive film. It is also to be understood that a fine powder of the materials described above may be dispersed in a carrier which may comprise silicone rubber, polyvinyl chloride (PVC) or the like to form the ion sensitive film 53.

In addition to the ion sensitive films referred to above, a porous film of synthetic fibre may be used as a carrier, which may be impregnated with the solution of a variety of ion exchange materials in a suitable solvent, with PVC mixed, and subsequently desicated to form an ion sensitive film which may also be effectively used in the present invention. By way of example, a solution of tetrahydrofuran (THF) and a small quantity of dioctyl adipate (DOA) as a plasticizer may be combined with a powder of PVC to provide a liquid material in which valinomycin as K+ exchange material may be dissolved. The resulting solution may be used to impregnate a porous film of synthetic fibre having a pore size of 0.1 to 3.0 μm and having its one surface coated with a conductive resin. Upon drying, a K+ sensitive film may be obtained.

Figure 2:
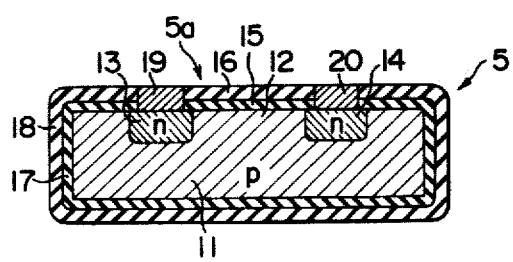
FIG. 2 is a cross section of a pH sensor used in the compound element of FIG. 1.

Referring to FIG. 2, the pH sensor 5 is shown in cross section. It comprises a silicon substrate 11 of p-type in which source and drain diffusion regions 13, 14 of n-type are formed with a gate 12 defined therebetween, thus providing an MOS transistor. An insulating layer 15 comprising silicon dioxide (SiO$_2$) is formed on at least the gate 12 of the transistor, and a H+ sensitive layer 16 which comprises SiN or Al$_2$O$_3$ is applied on top of the insulating layer 15 as by CVD process. When forming the insulating layer 15 and the H+ sensitive layer 16 on the gate 12, protective layers 17, 18 of the same material as these layers 15, 16 are simultaneously formed so as to cover the entire substrate 11. The well known vacuum evaporation and photoetching process may be used to provide electrode layers 19, 20 for contact with the source and the drain diffusion region 13, 14.

The purpose of the conductive resin 56 is to provide an electrochemical and physical connection between the ion sensitive film 53 and the insulated gate 5a of the pH sensor 5, and preferably comprises a material containing very fine silver particles.

The insulating resin 57 used should be one which effectively maintains a high insulation when immersed in a solution to be examined over an increased length of time. For example, silicone RTV rubber available from Shinetsu Chemical Co., or picene (C$_{22}$H$_{14}$) may be used.

In operation, when the ion sensitive film 53 is brought into contact with a solution to be examined, a potential difference is developed across the solution and the ion sensitive film 53 in accordance with the concentration of a specific ion contained in the solution. A contact potential is also developed across the film 53 and the conductive resin 56 as well as across the conductive resin 56 and the insulated gate 5a of the pH sensor 5, but remains constant. Hence, the potential difference which is developed across the interface between the solution to be examined and the ion sensitive film 53 according to the ion concentration is applied to the insulated gate 5a of pH sensor 5 through the conductive resin 56. By immersing a reference electrode in the solution to be examined and applying a suitable bias voltage thereto, a measurement of the source-drain current of the pH sensor 5 provides an indication of the concentration of the specific ion in the solution to be examined.

In the compound element 51, the material which provides an electrochemical connection between the ion sensitive film 53 and the insulated gate 5a of the pH sensor 5 comprises non-volatile and non-fluid conductive resin 56, which facilitates maintenance and control, and also allows a free choice of the orientation in which the element 51 is disposed, affording a great advantage that it can be easily handled.

Figure 3:
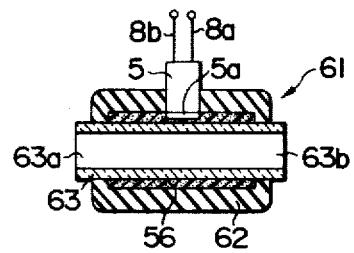
FIG. 3 is a cross section of a compound chemically sensitive element according to another embodiment of the invention which is constructed as an ion sensor through which a solution to be examined flows.

FIG. 3 shows another embodiment for a compound chemically sensitive element 61 which is constructed so that a solution to be examined flows through the element in order to determine the concentration of a specific ion therein. The compound element 61 shown comprises a highly insulating casing 62, a tubular ion sensitive film 63 disposed within the casing 62, a pH sensor 5 fixedly connected to the casing 62 with its insulated gate 5a located in opposing relationship with the outer periphery of the ion sensitive film 63, a conductive resin 56 disposed between the casing 62 and the ion sensitive film 63 so as to contact the insulated gate 5a, and a pair of lead wires 8a, 8b connected to the pH sensor 5.

The operation of the element 61 takes place in a manner such that a solution to be examined is introduced through an inlet 63a defined by one end of the ion sensitive film 63 and discharged through an outlet 63b defined by the other end thereof, thus allowing a determination of the concentration of a specific ion in the solution while the solution flows through the element.

In the embodiments described in connection with FIGS. 1 and 3, the compound chemically sensitive element is designed as an ion sensor which determines the concentration of a specific ion in a solution to be examined. However, it is to be understood that the compound element of the invention is not limited to an ion sensor, but is equally applicable to a chemical detecting element which detects a particular substance contained in a material to be examined.

Figure 4:
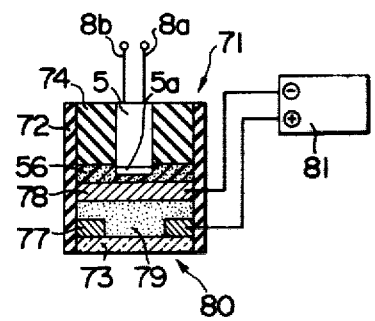
FIG. 4 is a cross section of a compound chemically sensitive element according to a further embodiment of the invention which is constructed as a glucose sensor.

FIG. 4 shows a compound chemically sensitive element according to a further embodiment of the invention which is adapted to determine the concentration of glucose contained in a solution to be examined. The element 71 shown comprises a highly insulating outer sleeve 72, a chemically sensitive film 73 applied to the lower end of the sleeve 72 so as to close the bottom opening thereof, a pH sensor 5 secured to the inside of the sleeve 72 with an insulating resin 74, with its insulated gate 5a located downside, an annular silver electrode 77 disposed in contact with the surface of the chemically sensitive film 73 which is located inside the sleeve 72, a plate-shaped platinum electrode 78 fixedly mounted within the sleeve 72 in spaced and opposed relationship with the silver electrode 77 to divide the interior of the sleeve 72 into a pair of upper and lower compartments, a conductive solid or gel-like electrolyte 79 such as lanthanum fluoride which fills the space between the platinum electrode 78 and the chemically sensitive film 73 and disposed in contact with the silver electrode 77, conductive resin 56 which fills the space between the platinum electrode 78 and the insulating resin 74 and disposed in contact with the insulated gate 5a of the pH sensor 5, and a pair of lead wires 8a, 8b connected to the pH sensor 5.

The chemically sensitive film 73 is formed by a gelled film comprising a porous support which is impregnated with polyacryl amide and glucose oxydase which is a glucose oxidizing enzyme.

In the compound element 71, the chemically sensitive film 73, the silver electrode 77, the platinum electrode 78 and the conductive solid or gel-like electrolyte 79 form together a chemically sensitive assembly 80, which has its platinum electrode 78 physically and electrochemically connected to the insulated gate 5a of the pH sensor 5 through the conductive resin 56.

In operation, when the chemically sensitive film 73 is brought into contact with a solution to be examined which contains glucose, the glucose oxydase contained in the film 73 acts to decompose the glucose into gluconic acid ($C_6H_{10}O_7$) and hydrogen peroxide ($H_2O_2$), and the amount of oxygen consumed depends on the concentration of the glucose. Consequently, by connecting the positive terminal of a constant current source 81 to the silver electrode 77 and the negative terminal to the platinum electrode 78 to form an oxygen electrode which is known in itself, the potential at the platinum electrode 78 varies in accordance with the change in the oxygen concentration of the chemically sensitive film 73. The change in the potential is applied to be the insulated gate 5a of the pH sensor 5 through the conductive resin 56, causing a change in the source-drain current thereof. Consequently, the resulting change in the current may be detected to determine the concentration of the glucose contained in a solution to be examined.

Figure 5:
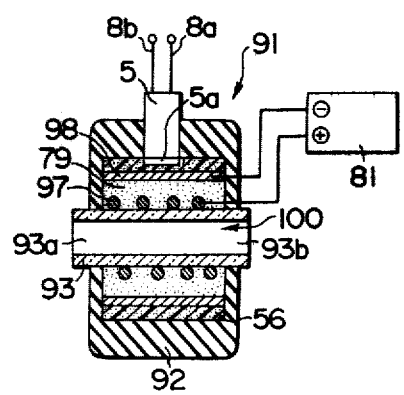
FIG. 5 is a cross section of a compound chemically sensitive element according to an additional embodiment of the invention which is constructed as a glucose sensor through which a solution to be examined flows.

FIG. 5 shows an additional embodiment of the invention in which the compound chemically sensitive element 71 of FIG. 4 is modified into a flow-through type. Specifically, the element 91 shown comprises a highly insulating casing 92, a tubular chemically sensitive film 93 disposed within the casing 92, a coil-shaped silver electrode 97 so as to be disposed around the film 93, a platinum electrode 98 disposed in spaced and surrounding relationship with the silver electrode 97 and having its opposite end openings secured to the sidewalls of the casing 92 so as to divide the interior thereof into a pair of compartments, a pH sensor 5 secured to the casing 92 with its insulated gate 5a disposed in opposing relationship with the outer peripheral surface of the platinum electrode 98, a conductive solid or gel-like electrolyte 79 disposed in contact with the silver electrode 97 between the chemically sensitive film 93 and the platinum electrode 98, conductive resin 56 which fills the space between the platinum electrode 98 and the casing 92 and disposed in contact with the insulated gate 5a, and a pair of lead wires 8a, 8b connected to the pH sensor 5.

It should be understood that the chemically sensitive film 93 is constructed in an identical manner as the chemically sensitive film 73 shown in FIG. 4. In the present embodiment, the chemically sensitive film 93, the silver electrode 97, the platinum electrode 98 and the conductive solid or gel-like electrolyte 79 form together a chemically sensitive assembly, generally in the same manner as in FIG. 4.

In operation, the positive terminal of a constant current source 81 is connected to the silver electrode 97 and the negative terminal to the platinum electrode 98 to form an oxygen electrode. A solution to be examined is introduced at an inlet 93a formed by one end of the chemically sensitive film 93 and discharged through an outlet 93b formed by the other end thereof, thereby permitting a determination of the concentration of glucose in the solution.

It should be understood that the invention is not limited to the specific embodiments described above, but that a number of changes, modifications and variations are possible therein. By way of example, in addition to constructing the compound element of the invention as an ion sensor or glucose sensor, it may be constructed as a gas sensor or a detecting element which determines the concentration of antigen or antibody.

What is claimed is:

1. A compound chemically sensitive element in which a potential difference developed across an interface between a solution to be examined and an ion sensitive assembly in accordance with the concentration of a specific ion contained in the solution is applied to an insulated gate of a pH sensor having an insulated gate field effect transistor structure, and in which a change in the source-drain current of the pH sensor is detected to determine the concentration of the specific ion in the solution, comprising an ion sensitive assembly, a pH sensor having an insulated gate field effect transistor structure, the sensor having an insulated gate and a conductive resin electrochemically connecting the assembly and insulated gate.

2. A compound chemically sensitive element according to claim 1, in which the ion sensitive assembly comprises a film of soda aluminosilicate glass.

3. A compound chemically sensitive element according to claim 1, in which the ion sensitive assembly comprises a solid film formed by a mixture of silver chloride and silver sulfide.

4. A compound chemically sensitive element according to claim 1, in which the ion sensitive assembly comprises a solid film of lanthanum fluoride.

5. A compound chemically sensitive element according to claim 1, in which the ion sensitive assembly comprises a porous film of synthetic fibre impregnated with an ion exchange material and polyvinyl chloride.

6. A compound chemically sensitive element according to claim 1 in which the ion sensitive assembly comprises a semiconductor substrate of one of the p and n conductivity types, a pair of spaced apart surface layers of the other of the p and n conductivity type formed on the surface of the semi-conductor substrate, an insulated gate film comprising at least one layer extending on an upper surface of a channel region between the pair of spaced apart surface layers and on their upper surfaces; in which the conductive resin is in contact with the insulated film gate; and in which the ion sensitive assembly is a film in contact with the conductive resin.

7. A compound chemically sensitive element according to claim 1 having an intermediate layer disposed between the conductive resin and the ion sensitive assembly, the intermediate layer comprising a pair of electrodes in spaced and opposed relationship to each other interconnected by an electrolyte.

8. A compound chemically sensitive element according to claim 7 having a constant current source which has a positive and negative terminal, wherein the pair of electrodes are a silver electrode and a platinum electrode connected to the positive and negative terminal of the constant current source so as to form an oxygen electrode across which potential differences are developed in accordance with the amount of oxygen consumption at the chemically sensitive assembly in a manner corresponding to the concentration of a specific substance contained in a material to be examined and in which the potential differences applied to the insulated gate to cause a change in the source-drain current of the pH sensor, which change is detected to determine the concentration of the specific substance in the material.

9. A compound chemically sensitive element according to claim 8 in which the chemically sensitive assembly contains polyacryl amide and glucose oxidase.

10. A compound chemically sensitive element according to claim 1 or 7 in which the conductive resin contains silver particles.

11. A compound chemically sensitive element according to claim 7 in which the chemically sensitive assembly comprises a chemically sensitive film, a silver electrode disposed in contact with the chemically sensitive film, a platinum electrode disposed in spaced and opposing relationship with the silver electrode, and a conductive solid or gel-like electrolyte which fills the space between the platinum electrode and the chemically sensitive film and disposed in contact with the silver electrode, the platinum electrode being electrochemically connected to the insulated gate of the pH sensor through the conductive resin.

12. A compound chemically sensitive element according to claim 11 in which the chemically sensitive film comprises a gelled film formed of an impregnated polyacryl amide and glucose oxydase porous support, whereby the chemically sensitive film is selectively sensitive to glucose contained in the material to be examined.

13. A compound chemically sensitive element according to claim 1 or 11 in which the ion sensitive assembly or the chemically sensitive film is tubular in configuration to permit the solution or the material to be examined to flow therethrough, whereby the assembly or the film is selectively sensitive to the specific ion in the solution or to the specific substance in the material to be examined.

14. A compound chemically sensitive element according to claim 1 or 7 in which the pH sensor comprises an MOS transistor having a gate insulating layer formed by a silicon dioxide layer upon which is a $H^+$ sensitive layer which comprises a silicon nitride layer or an aluminium oxide layer which is selectively sensitive to hydrogen ion.

* * * * *